United States Patent
De Sousa

[11] Patent Number: 5,972,290
[45] Date of Patent: Oct. 26, 1999

[54] PROCESS AND EQUIPMENT FOR THE PROGRAMMED SCENTING OF ENVIRONMENTS

[76] Inventor: Mauricio De Sousa, R. do Curtume, 745 BL.F, Sao Paulo, Brazil, 05065-001

[21] Appl. No.: 08/834,939

[22] Filed: Apr. 7, 1997

[30] Foreign Application Priority Data

Apr. 9, 1996 [BR] Brazil ............................. PI 9601523-3

[51] Int. Cl.⁶ ................................. A61L 9/02; A61L 9/03
[52] U.S. Cl. ................................. 422/5; 422/4; 422/123; 422/124; 422/125; 422/305; 422/306
[58] Field of Search ................................. 422/4, 5, 120, 422/123, 124, 305, 306, 125; 239/57, 60

[56] References Cited

U.S. PATENT DOCUMENTS

| | | | |
|---|---|---|---|
| 4,556,539 | 12/1985 | Spector | 422/5 |
| 4,603,030 | 7/1986 | McCarthy | 422/4 |
| 4,905,112 | 2/1990 | Rhodes | 422/124 |
| 5,023,020 | 6/1991 | Machida et al. | 422/124 |
| 5,069,876 | 12/1991 | Oshinsky | 422/4 |
| 5,178,327 | 1/1993 | Palamand et al. | 239/57 |
| 5,273,690 | 12/1993 | McDowell | 422/124 |
| 5,342,594 | 8/1994 | Sarkomaa | 423/244.08 |
| 5,565,148 | 10/1996 | Pendergrass, Jr. | 422/124 |
| 5,734,590 | 3/1998 | Tebbe | 364/400.01 |

FOREIGN PATENT DOCUMENTS

| | | |
|---|---|---|
| 0295129 | 12/1998 | European Pat. Off. . |
| 2553666 | 4/1985 | France . |
| 2249958 | 5/1992 | United Kingdom . |
| 2256589 | 12/1992 | United Kingdom . |

*Primary Examiner*—Elizabeth McKane
*Assistant Examiner*—Fariborz Moazzam
*Attorney, Agent, or Firm*—Loeb & Loeb LLP

[57] ABSTRACT

A process and apparatus for the programmed scenting of environments, comprising the steps of piercing a capsule containing a fragrant substance and dispersing a sequence of the fragrances throughout the environment in synchronization with an event being held. The event can be any live, recorded, or pre-programmed performance, including motion pictures, television episodes, computer games, or stage plays. The fragrances dispersed into the environment derive from capsules of scenting substances and compounds embedded on a disk and pierced in synchronization with the actions, places, and motions being executed.

10 Claims, 3 Drawing Sheets

PROCESS AND EQUIPMENT FOR THE PROGRAMMED SCENTING OF ENVIRONMENTS

BACKGROUND OF THE INVENTION

1. Field of the Invention

The present invention pertains to a process and apparatus for the programmed scenting of environments. Specifically, the present invention pertains to a process and apparatus to scent environments in synchronization with an event being held.

2. Description of Related Art

Devices for scenting of environments are highly diversified and widely commercialized. Examples include aerosol containers, sticks or tablets for the scenting of bathrooms, and equipment affixed to toilets and urinals. These devices are available in a wide variety of fragrances, such as violet, wild flower, tutti-frutti, green apple, and others.

Further known methods and devices for the scenting of environments are designed to release different fragrances in a pre-determined sequence. An example U.S. Pat. No. 5,069,876 (issued Dec. 3, 1991), which describes a display unit for the sales of products in which the display unit incorporates sound equipment associated with a scent release device. The device can also be connected to a photographic display unit, which can be pre-programmed. The French patent publication FR 2,553,666 (dated Apr. 26, 1985) pertains to a portable device for the release of perfume fragrances together with images and sound. U.S. Pat. No. 4,603,030 (issued Jul. 29, 1986) pertains to a system for the release of a variety of fragrances in response to a pre-determined sequence and timing. The European patent publication EP 0295129 (dated Dec. 14, 1988) describes a method and apparatus for the release of various fragrances into an environment from different storage containers according to a determined rate of time controlled by a timer. U.S. Pat. No. 5,342,594 (issued Aug. 30, 1994) describes a device equipped with a cartridge impregnated with a fragrance and operated by a battery for the release of at least two different scents. U.S. Pat. No. 5,273,690 (issued Dec. 28, 1993) describes a device employing forced air together with a vehicle loaded with a variety of fragrances placed in individual cells. These cells have breakable walls for releasing the scent into the forced air current. U.S. Pat. No. 5,178,327 (issued Jan. 12. 1993) describes a device for scenting environments, including an array of different aromas that are selected through the means of a rotating cylinder or disk. The UK patent publication 2256589 (issued Dec. 16, 1992) pertains to a device for the scenting of environments with multiple compartments for different aromas. The UK patent publication 2249958 (issued May 27, 1992) describes a device for the generation of aromas which are selected from a distance by the user.

Nevertheless, no efficient process has been proposed to promote the scenting of environments in synchronization with an event at the time of its performance.

SUMMARY OF THE DISCLOSURE

It is an object of embodiments of the invention to provide for the scenting of environments in synchronization with an event simultaneously being performed.

Another object of embodiments of the present invention is to provide a process for the scenting of environments, preferably closed environments, such as television, video and CD-ROM rooms, movie houses, theaters and show rooms, whereby the scenting is in synchronization with the event at the time of its performance.

According to one aspect of the present invention, a process is provided through which an environment is scented with several different fragrances, in sequence and specifically in agreement with the event's script, such as a motion picture, a stage play, or a show. The fragrance is diffused throughout the environment in which the event is being presented, so as to enhance the reality of the scene or image.

A second aspect of the present invention is to provide an apparatus for the fulfillment of the aforementioned process, including a delivery device equipped with several individual compartments containing various fragrances to be dispersed throughout the environment.

DETAILED DESCRIPTION OF THE PREFERRED EMBODIMENTS

Accordingly, embodiments of the present invention provide a process and apparatus for the scenting of environments, preferably enclosed ones, through which a sequence of fragrances are dispersed into the environment, synchronized with an event that is being performed, such as a motion picture or other prerecorded video, a stage play or a show and/or musical. The sequence of the fragrances that are to be dispersed into the environment will be accomplished through the means of a carrier of scenting substances or compounds that will be operated in tune with the beginning of the event and synchronized with the action, places and movements that are unfolding throughout the event. This characteristic will afford the audience a feeling of greater reality during the various scenes beheld, because they will have within their olfactory sense of scent that is characteristic of the location in each of the respective scenes.

The scenting substances and compounds to be employed in the process, according to the present invention, must be produced or formulated in agreement with the established standards for this type of product which will be inhaled by people. Therefore, they must be non toxic, anti-allergic, non irritant and as inert as possible in relation to the environment. A large number of possible formulations can be used in the process of embodiments of the present invention including, but not limited to formulations containing those scents that emulate common every day odors that are sensed, such as the smell of the rain, wet soil, garden flowers, dust, forests, etc. Such odoriferous substances or compounds can be formulated as dust, granules or liquids, and therefore, must be conveniently contained according to its nature. The containers must be individually packed and filled with the appropriately defined quantity of scenting substance or compound, in order that they may be easily broken in the established sequence to supply the scent during a previously established and defined period of time. In a preferred embodiment the containers are in the form of fragrance capsules made of puncturable plastic or other suitable material, filled with odoriferous substances as discussed above.

Figure 1:
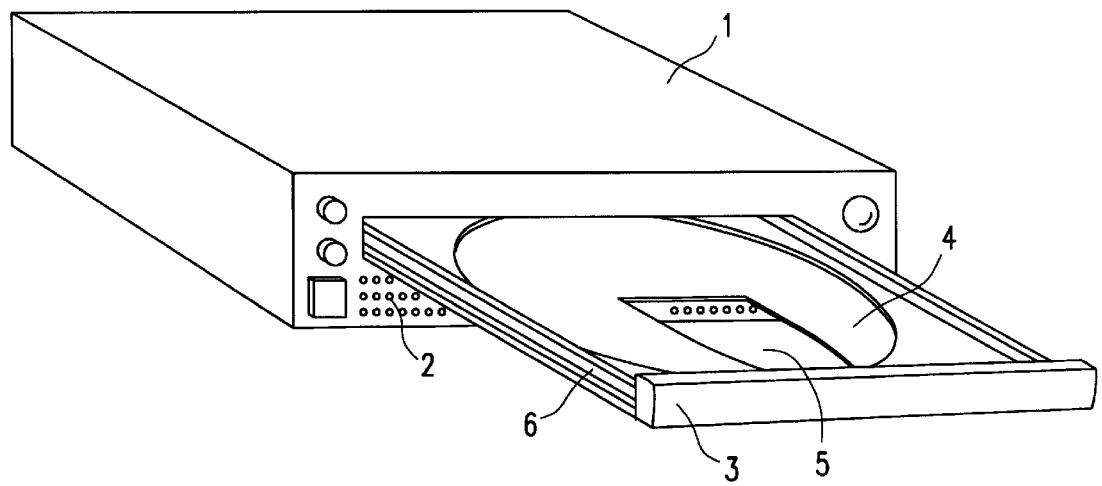
FIG. 1 is a perspective view of a preferred embodiment of an apparatus for scenting an environment.
Figure 2:
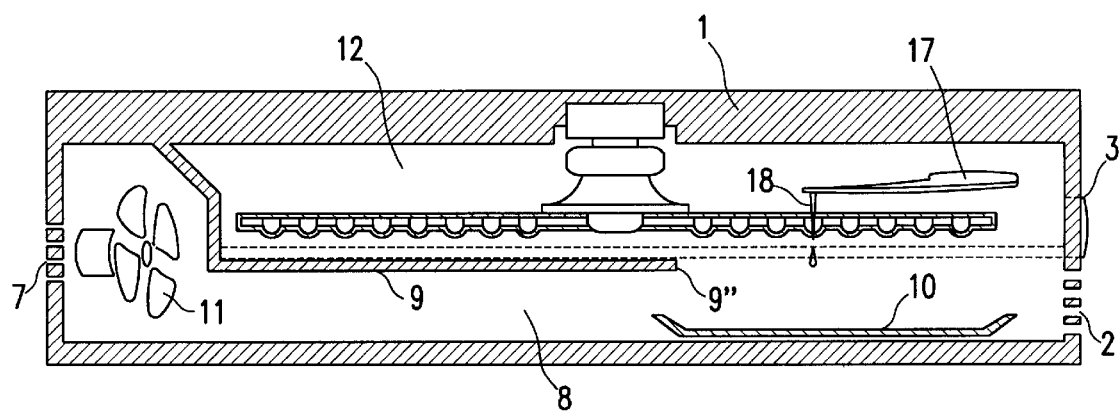
FIG. 2 is a schematic side view of the interior of the apparatus of FIG. 1.
Figure 3:
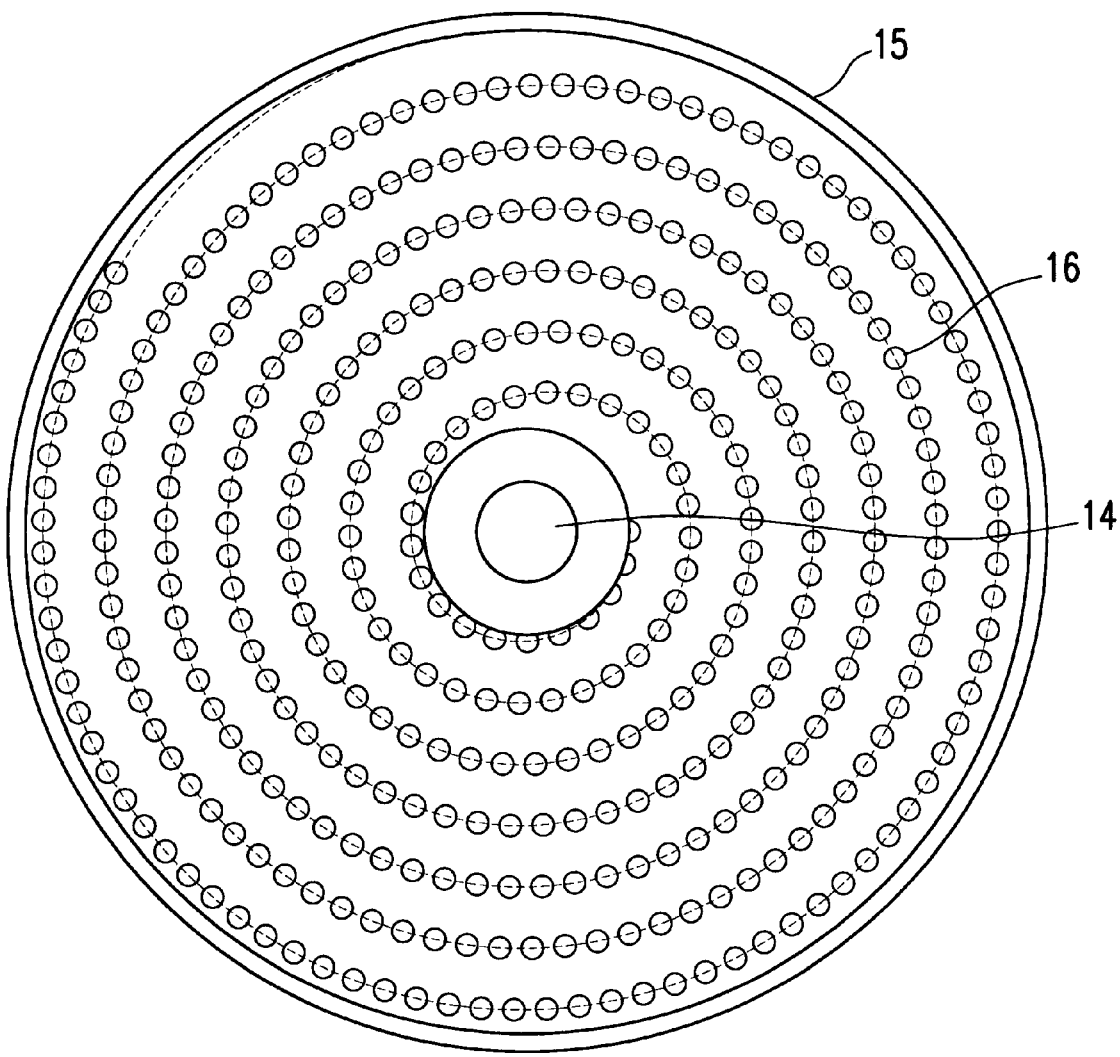
FIG. 3 is a top plan view of a preferred embodiment of a disk embedded with fragrance carrying capsules.

FIGS. 1, 2 and 3 show an example of the present invention, in which a disk 15 (FIG. 3) containing multiple fragrance capsules may be inserted into a disk processing box 1 (FIG. 1) for selectively releasing and dispensing scents. The box 1 is square or rectangular shape, with a series of small orifices in front 2 disposed substantially throughout its length with another series of small orifices in the back 7. Above these orifices 2 a moveable drawer is provided 3 with a circular indentation 4, and a hollowed out opening section 5. The moveable drawer is provided with lateral guides 6, so that it may slide between opened and closed positions (FIGS. 1 and 2, respectively).

The interior of the box 1 contains a lower compartment 8 and an upper compartment 12. The upper and lower compartments are separated by a corner plate 9, which extends from the rear of said box 1 until an intermediate section 9", forming a sort of channel in said compartment 8 and the housing for a disk processing mechanism. The lower compartment 8 has a rear space in which a small fan 11 is installed, for directing air toward a container 10 located in the forward section of the compartment 8.

The disk processing mechanism is of the kind that fits into a center orifice 14 of a disk 15 bearing small capsules of fragrances 16. The disk processing mechanism 13 operates with a perforation device 17 that is moveable by drive means (not shown) in a vertical direction and is equipped with a pointed element 18 that serves to selectively puncture the capsules 16 containing the fragrances. Therefore, these capsules 16 must be manufactured from an appropriate material that is suitable to be punctured by this pointed element 18.

The equipment described above is electronic and operates by commands received from a video tape, compact disc, or computer program. Thus a disk 15 containing a determined sequence of fragrance capsules 16, previously programmed in tune with the event, a motion picture, or a show, is conveniently inserted into the drawer 3, which is immediately closed. The equipment is turned on at the beginning of the event, and then in synchronization with the sequence of the scenes that are being shown, and whenever a specific fragrance is required, the mechanism turns the disk 15 and places the respective fragrance capsule that is required under the device 17, in order that with an up and down vertical motion of device 17, capsule 16 is pierced with the pointed element 18. At that instance, the scenting substance or compound contained in the foregoing capsule 16 is released into the container 10. The small fan 11 turns on, drawing air through the small rear orifices 7 producing a draft in compartment 8 under plate 9 for dispersing the fragrance through the small forward orifices 2. In this fashion the fragrance is released into the environment in which the event is being held, spreading throughout the environment and thereby creating an atmosphere of reality for the audience. This procedure is repeated by the equipment, which will select the capsule to be punctured for the next scene in which a specific fragrance is required.

The fragrance's persistence can be controlled, for instance, by the very chemical formulation previously produced for the respective event. Also, the duration of the fragrance can be controlled through odor inhibiting agents, such as chemical inhibitors, which may be included in, the set of capsules 16. Thus, each event shall have its disk with the corresponding sequences of fragrances. However, this does not exclude the introduction of random scents for a specific event.

The operation of the equipment as a whole, or be it, the mechanism, perforation device 17 and fan 11, are controlled by electronic commands that are inaudible to the audience. By the same token, the medium of these elements are such as not to produce any strange sounds or undesirable noises perceptible during the event. In preferred embodiments, suitable electronic control apparatus (not shown) is provided for controlling the operation of mechanism, selectively rotating the disk and containing the perforation device 17. The control apparatus may be responsive to a timer for releasing scents in predetermined time periods, timed from, for example, the initiation of the event. Alternatively, the control apparatus may be responsive to synchronization signals produced during the event. Such signals may be recorded on the medium on which the event is recorded or may be produced independent of the event and transmitted electronically, electromagnetically or optically to the control apparatus. Suitable electronic apparatus capable of controlling the operation of mechanism would be within the scope of one skilled in the art.

The process and the equipment, according to embodiments of the present invention can be produced for a variety occasions. Thus, for instance, such processes and equipment may be provided for already existing movies and programmed so that they may be synchronized with the sequences of the scenes; old movies may be reissued with signals for the synchronization of the equipment; or tapes or other recording media may incorporate the signals for the synchronization with the equipment.

The disks produced can be disposable or returnable to be re-filled, by refilling them with the respective fragrance capsules, which are specifically related to the corresponding motion picture.

Figure 4:
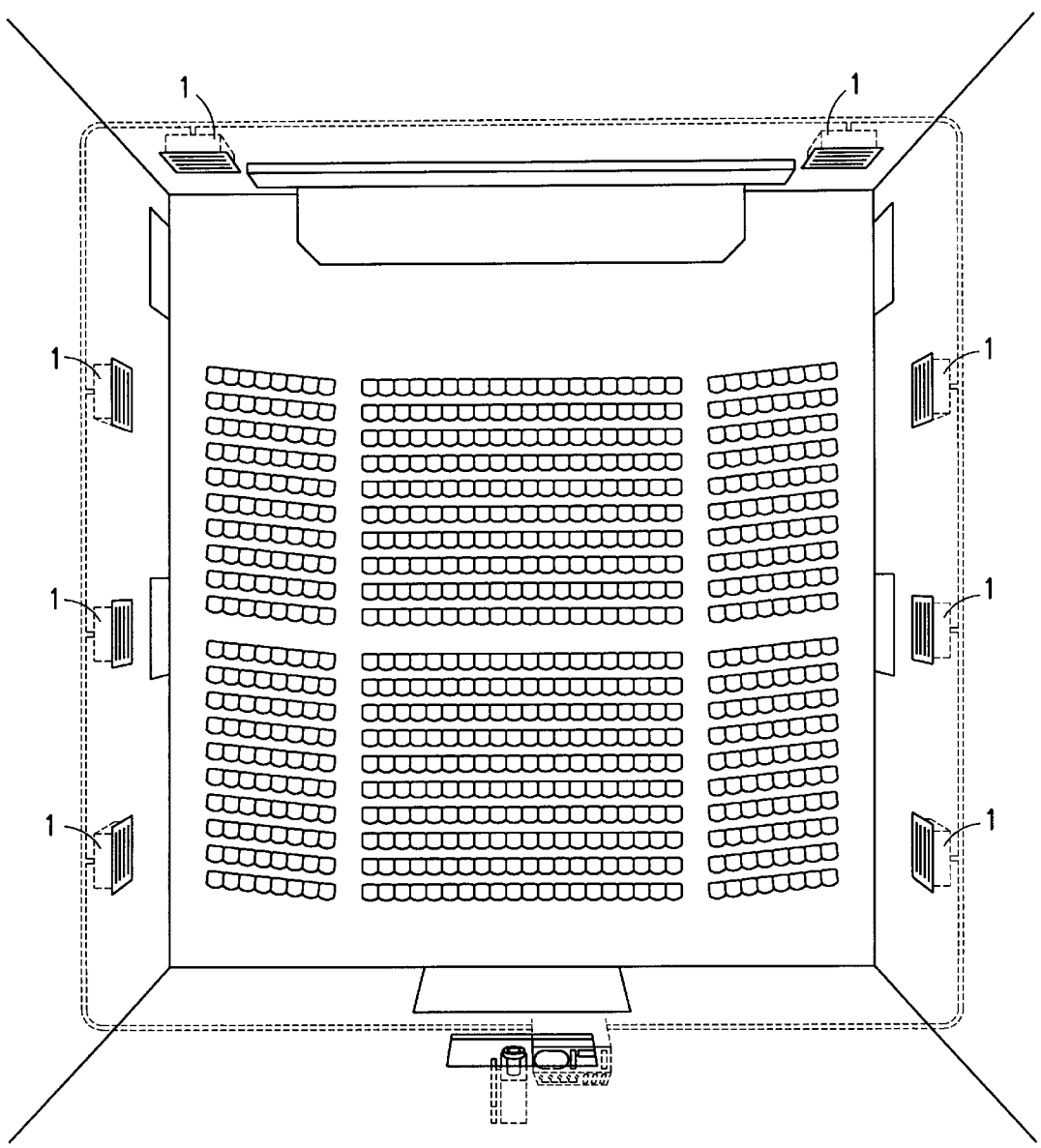
FIG. 4 is a top plan view of a theater equipped with several preferred embodiments of the apparatus.

According to preferred embodiments of the present invention, the apparatus is relatively small and can be installed, for example, side by side with a television set, video cassette recorder, or computer. As shown in FIG. 4, several units of the apparatus 1 can be installed in larger environments such as movie theaters, where they can be operated simultaneously with similar or identical disks. The apparatus can be incorporated in a television set, in a manner similar to the incorporation of video cassette recorders.

What is claimed is:

1. A method for dispensing a sequence of fragrance into a room tuned to and synchronized with an event, said method comprising:

sequentially selecting at least one capsule of a set of fragrance filled capsules in response to an electronic signal associated with the event, said capsules being disposed on a turning disk inside a housing;

opening said at least one capsule thereby releasing the fragrance therefrom;

dropping the fragrance of said capsule on a receptacle located below said turning disk; and creating an air current inside said housing, whereby said fragrance is dispensed outwards of the housing into said room.

2. A method according to claim 1, characterized in that said capsules are opened by perforation.

3. A method according to claim 1, characterized in that said air current is created by means of a fan located inside housing.

4. A method according to claim 1, characterized in that said capsules are opened in response to an electronic signal received from at least of a video tape, a CD rom disk and from softwear from a microcomputer.

5. A method according to claim 2, characterized in that said capsules are opened in response to an electronic signal received from at least one of a video tape, a CD rom disk and from softwear from a microcomputer.

6. A method according to claim 3, characterized in that said capsules are opened in response to an electronic signal received from at least one of a video tape, a CD rom disk and from softwear from a microcomputer.

7. An apparatus for dispensing a sequence of fragrances into a room tuned to and synchronized with an event, said apparatus comprising:

a means for producing an electronic signal;

a housing having a first half and second half opposite to said half, with each said half having at least one bore therethrough;

a moveable receptable in said housing, said moveable receptable having a hollowed out portion;

a turning disk supported by said moveable receptable, said disk carrying a set of fragrance-filled capsules and rotatable in response to the electronic signal;

an opening means for opening a predetermined capsule when said capsule is above said hollowed out portion;

a stationary receptable below said moveable receptable, said stationary receptacle receiving the fragrance dropped from the capsule; and a fan facing said stationary receptacle, said fan activating upon receipt of the electronic signal and dispensing said fragrance through said at least one bore of the first half.

8. An apparatus according to claim 7, characterized in that said opening means comprises a pointed element, said pointed element being moveble in a vertical direction above said disk.

9. An apparatus according to claim 7, characterized in that said housing is divided into upper and lower compartments by a plate that extends from said second half towards said first half.

10. An apparatus according to claim 9, characterized in that said moveable receptable and said turning disk are located in said upper compartment, while said stationary receptable and said fan are located in said lower compartment.

* * * * *